United States Patent
Tung et al.

(10) Patent No.: US 9,228,939 B2
(45) Date of Patent: Jan. 5, 2016

(54) REFRACTIVE FUEL CONCENTRATION DETECTOR

(75) Inventors: Chun-Chin Tung, Chu Pei (TW); Yung-Lieh Chien, Chu Pei (TW)

(73) Assignee: PRICEPLAY TAIWAN INC., Taipei (TW)

(*) Notice: Subject to any disclaimer, the term of this patent is extended or adjusted under 35 U.S.C. 154(b) by 2135 days.

(21) Appl. No.: 11/744,563

(22) Filed: May 4, 2007

(65) Prior Publication Data

US 2007/0264545 A1 Nov. 15, 2007

(30) Foreign Application Priority Data

May 15, 2006 (TW) ................................ 95117176 A

(51) Int. Cl.
*H01M 8/04* (2006.01)
*G01N 21/41* (2006.01)
*G01N 21/3577* (2014.01)
*G01N 21/35* (2014.01)
*H01M 8/10* (2006.01)

(52) U.S. Cl.
CPC ........ *G01N 21/4133* (2013.01); *G01N 21/3577* (2013.01); *G01N 21/35* (2013.01); *G01N 2021/4153* (2013.01); *H01M 8/04194* (2013.01); *H01M 8/1011* (2013.01)

(58) Field of Classification Search
CPC .......... H01M 8/04194; G01N 21/4133; G01N 2021/4153
USPC ................................... 356/128, 343; 429/449
See application file for complete search history.

(56) References Cited

U.S. PATENT DOCUMENTS

| | | | | | |
|---|---|---|---|---|---|
| 4,672,216 | A | * | 6/1987 | Pitt et al. | 250/574 |
| 4,710,643 | A | * | 12/1987 | Schmukler et al. | 250/573 |
| 5,305,071 | A | * | 4/1994 | Wyatt | 356/73 |
| 5,548,393 | A | * | 8/1996 | Nozawa et al. | 356/70 |
| 6,306,285 | B1 | * | 10/2001 | Narayanan et al. | 205/787 |
| 6,549,276 | B1 | * | 4/2003 | Longtin | 356/128 |
| 6,573,992 | B1 | * | 6/2003 | Drake | 356/338 |
| 6,815,682 | B2 | * | 11/2004 | Rabinovich et al. | 250/338.5 |
| 6,975,392 | B2 | * | 12/2005 | Larkin | 356/246 |
| 7,027,138 | B2 | * | 4/2006 | Larkin et al. | 356/128 |
| 7,221,440 | B2 | * | 5/2007 | McCann et al. | 356/128 |
| 7,294,513 | B2 | * | 11/2007 | Wyatt | 436/45 |
| 7,471,379 | B2 | * | 12/2008 | Chiarello et al. | 356/136 |
| 7,816,045 | B2 | * | 10/2010 | Oishi et al. | 429/428 |
| 8,228,489 | B2 | * | 7/2012 | Suzuki et al. | 356/128 |
| 2003/0124398 | A1 | * | 7/2003 | Rabinovich et al. | 429/13 |
| 2006/0141307 | A1 | * | 6/2006 | Ryoichi et al. | 429/24 |
| 2006/0222915 | A1 | * | 10/2006 | Sumino et al. | 429/22 |
| 2007/0059589 | A1 | * | 3/2007 | Arasawa | G01N 21/05 429/90 |
| 2008/0002200 | A1 | * | 1/2008 | White et al. | 356/339 |
| 2009/0269625 | A1 | * | 10/2009 | Odgaard et al. | 429/13 |
| 2011/0053024 | A1 | * | 3/2011 | Nishimura et al. | 429/432 |

* cited by examiner

*Primary Examiner* — Erick Solis
(74) *Attorney, Agent, or Firm* — Muncy, Geissler, Olds & Lowe, P.C.

(57) ABSTRACT

A refractive fuel concentration detector comprises mainly a light source device and a light-sensing device. The light source device supplies light source incident on the fuel and refracts light source to the light-sensing device such that a plurality of light sensor therein would respectively output a corresponding electrophysical quantity signal based on the light quantity received. Moreover, a circuit means can be used to obtain concentration information of fuel based on the electrophysical quantity signal output by the light sensors and the tag information of those light sensors.

16 Claims, 8 Drawing Sheets

REFRACTIVE FUEL CONCENTRATION DETECTOR

FIELD OF THE INVENTION

The present invention relates to a refractive fuel concentration detector, particularly a mechanism for obtaining fuel concentration through change of optical properties and devices thereof.

BACKGROUND OF THE INVENTION

Conventional fuel cells undergo electrochemical reaction with hydrogen-rich fuel (e.g. methanol) and oxygen fuel. In the applications of such fuel cells, it is necessary for users to know when to replenish the fuel when fuel concentration or level becomes low. Detection of fuel concentration in the fuel container is typically achieved through expensive metering sensor, which is rather uneconomical when used extensively in portable electrical products.

In light of the drawbacks of conventional fuel cells, the inventor aims to develop a refractive fuel concentration detector.

SUMMARY OF THE INVENTION

The primary object of the invention is to provide a refractive fuel concentration detector that can further obtain fuel concentration by detecting change in the optical properties of fuel in the fuel cell.

Another object of the invention is to provide a refractive fuel concentration detector that achieves detection of fuel concentration by installing a fuel concentrator detector in the fuel accommodation space of fuel cell.

A further object of the invention is to provide a refractive fuel concentration detector that achieves detection of fuel concentration by installing a fuel concentration detector in the fuel channel of fuel cell.

To achieve the aforesaid objects, the present invention provides a refractive fuel concentration detector comprising a light source device and a light-sensing device. The light source device supplies light source incident onto fuel and refracts the light source to the light-sensing device such that a plurality of light sensor therein would respectively output a corresponding electrophysical quantity signal based on the light quantity received. Furthermore, a circuit means can be used to obtain concentration information of fuel based on the electrophysical quantity signal output by the light sensors and tag information of light sensors.

The objects, features and effects of the invention are described in detail below with embodiments in reference to the accompanying drawings.

DETAILED DESCRIPTION OF THE INVENTION

Figure 1:
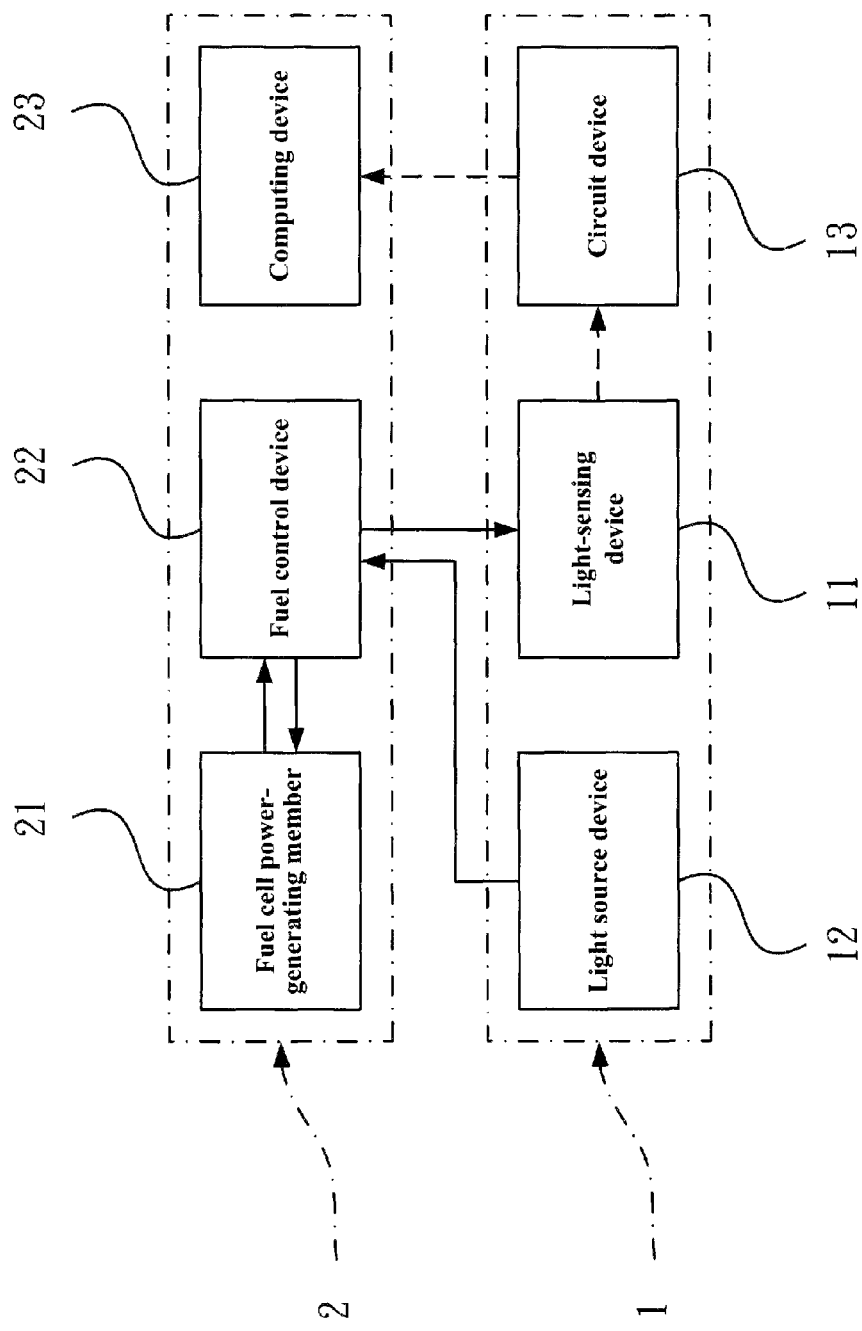
FIG. 1 is a diagram showing the relations of the components in the refractive fuel concentration detector according to the invention.

Referring to FIG. 1 which shows the relations of the components in the refractive fuel concentration detector according to the invention, the invention pertains to a concentration detector (1) that can be used in a fuel cell system (2). The concentration detector (1) comprises a light-sensing device (11), a light source device (12), and a circuit device (13). The light-sensing device (11) consists of a plurality of light sensors, each light sensor using photosensitive element to convert optical signal into electrical signal. Under illumination, each light sensor could output a corresponding current value or another electrical signal based on the dose of light received. The light source device (12) supplies source of light, which is infrared light, visible light or single-frequency light. The circuit device (13) captures the current value output by each light sensor corresponding to the illumination state, and outputs an electrical signal carrying the current value signal. Moreover, the fuel cell system (2) comprises a fuel cell power-generating member (21), a fuel control device (22), and a computing device (23). The fuel cell power-generating member (21) is an energy converter containing catalyst that can undergo electrochemical reaction with hydrogen-rich fuel and oxygen fuel, and furthermore, convert chemical energy into electrical energy for output. The fuel control device (22) stores and transports fuel needed for the electrochemical reaction of fuel cell system (2) and residual solution after the reaction. The computing device (23) has logic computing means to process electrical signals output by the light-sensing device (11) and computes corresponding fuel concentration information.

The circuit device (13) and the computing device (23) can be integrated into a circuit means. Such circuit means can capture the current value output by each light sensor corresponding to the state of illumination, and based on which, compute and obtain the corresponding fuel concentration information. The circuit means can further be an integrated circuit means. The computing device (23) is an integrated circuit component, such as a microprocessor or CPU.

The light source device (12) can further contain an optical path guide mechanism to direct the path of light source and the direction of emission.

Figure 2:
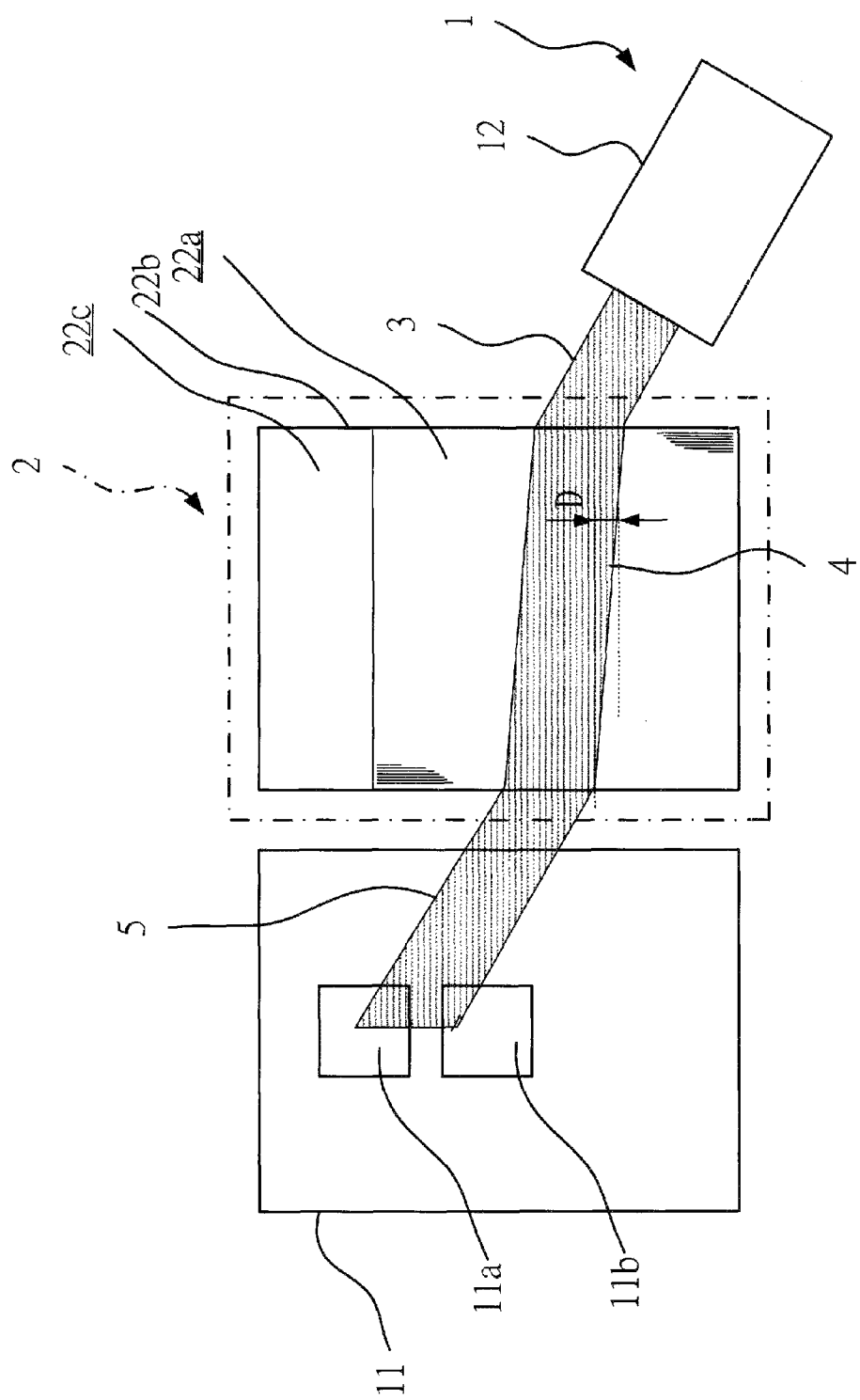
FIG. 2 is a schematic diagram showing the component layout and the first state of the refractive fuel concentration detector according to a first embodiment of the invention.
Figure 3:
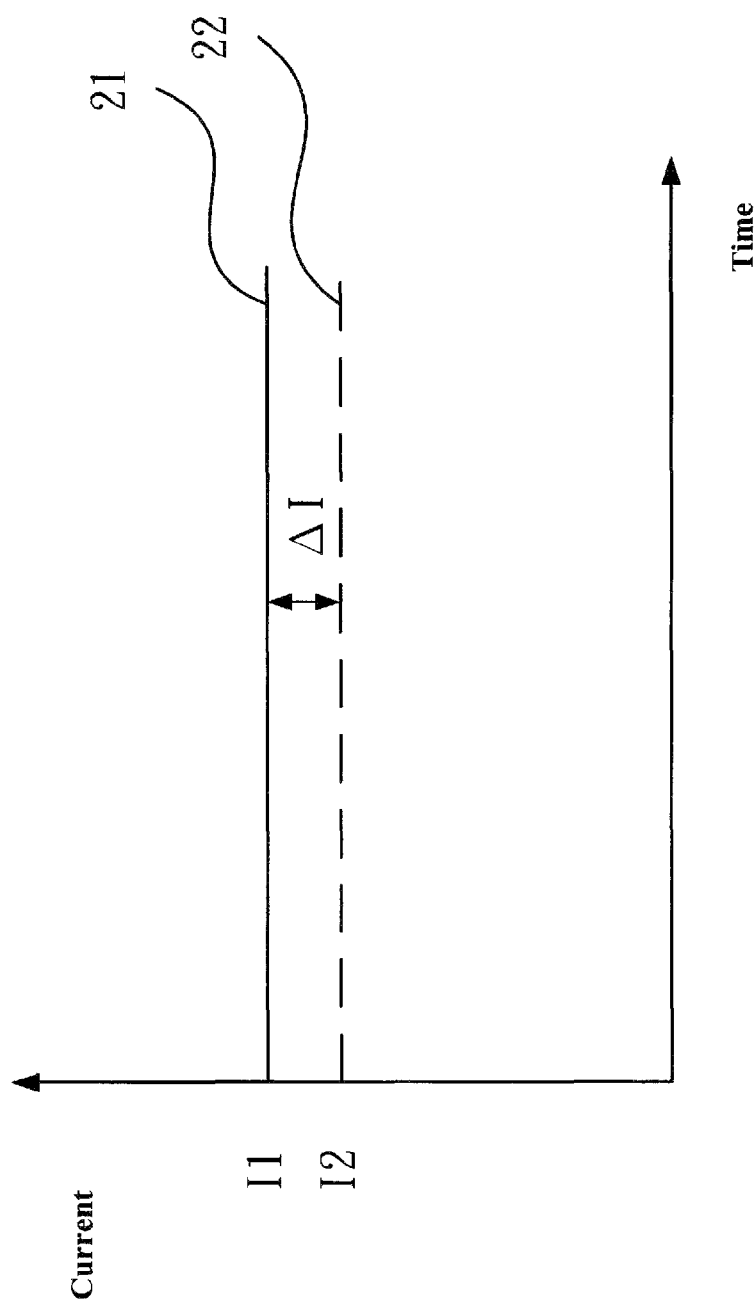
FIG. 3 is a diagram showing the first state signal output of the refractive fuel concentration detector according to a first embodiment of the invention.

FIG. 2 is a schematic diagram showing the component layout and the first state of the refractive fuel concentration detector according to a first embodiment of the invention. FIG. 3 is a diagram showing the first state signal output of the refractive fuel concentration detector according to a first embodiment of the invention. Referring to FIG. 2 and FIG. 3, in the light-sensing device (11), the plurality of light sensors include a first light sensor (11a) and a second light sensor (11b). The light source device (12) supplies infrared light. A part of the fuel control device (22) in the fuel cell system (2) is defined as a detecting member (22a), the detecting member (22a) containing fuel in the fuel control device (22). The light-sensing device (11) and the light source device (12) are disposed at each side of detecting member (22b). The light source device (12) supplies an incident light (3) from an infrared light source to enter the detecting member (22b). Following the Snell's law, the incident light (3) penetrates the fuel (22a) in the detecting member (22b) to form a first refracted light (4). The first refracted light (4) again follows the Snell's law to pierce through the fuel (22a) and form a second refracted light (5). The second refracted light (5) projects on the light-sensing device (11) to enable the first light sensor (11a) and the second light sensor (11b) to receive respectively a specific dose of light. When the concentration of fuel (22a) is in a first state, the first refracted light (4) forms a displacement D in the fuel (22a) such that the first light sensor (11a) and the second light sensor (11b) would respectively output a corresponding current 11 and current 12 based on the dose of light received. The circuit device (13) obtains and outputs electrical signals carrying the current value signals. Subsequently, the computing device (23) of the fuel cell system (2) determines the concentration value of fuel (22a) in the first state based on the electrical signals of current value signals.

Figure 4:
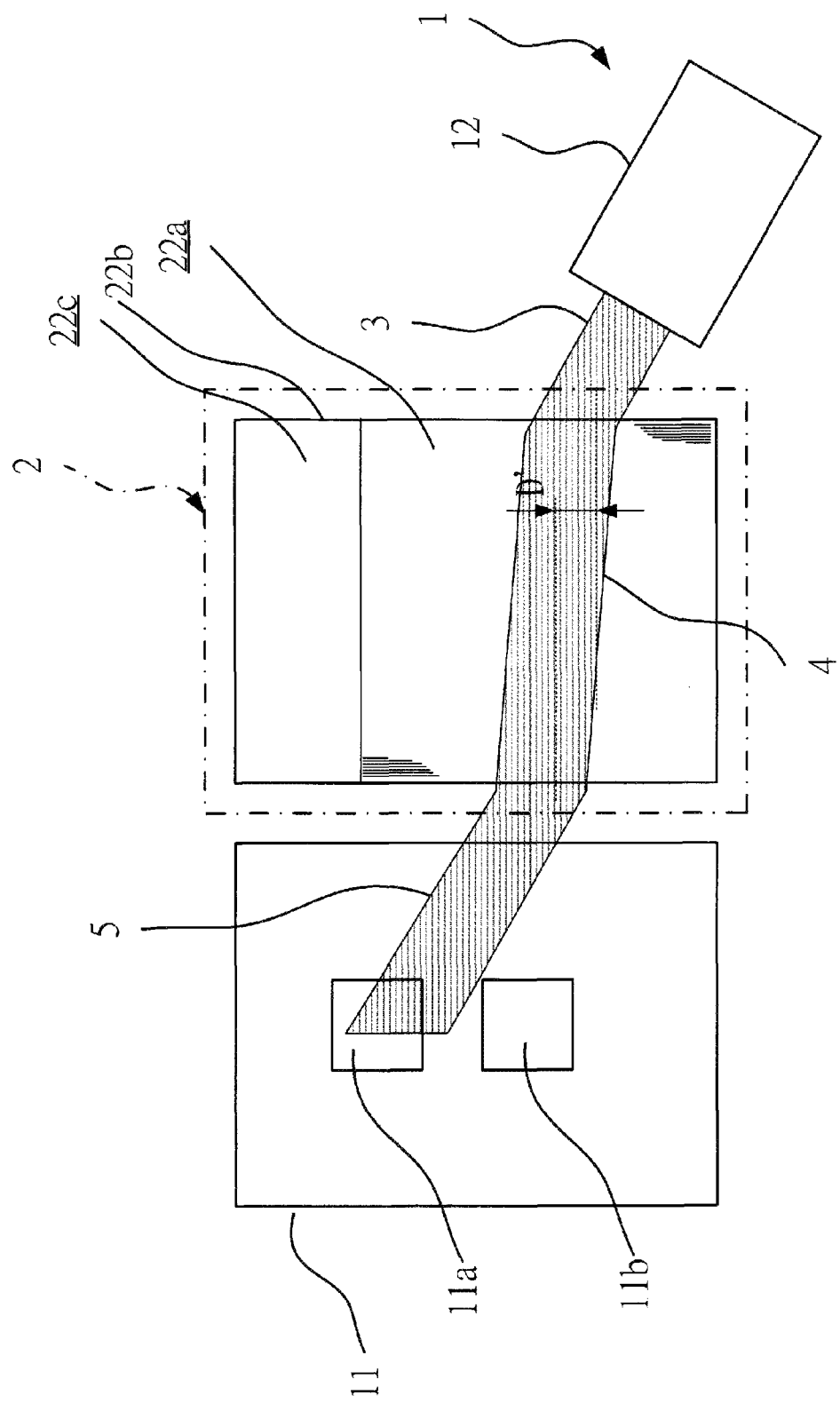
FIG. 4 is a schematic diagram showing the component layout and the second state of the refractive fuel concentration detector according to a first embodiment of the invention.
Figure 5:
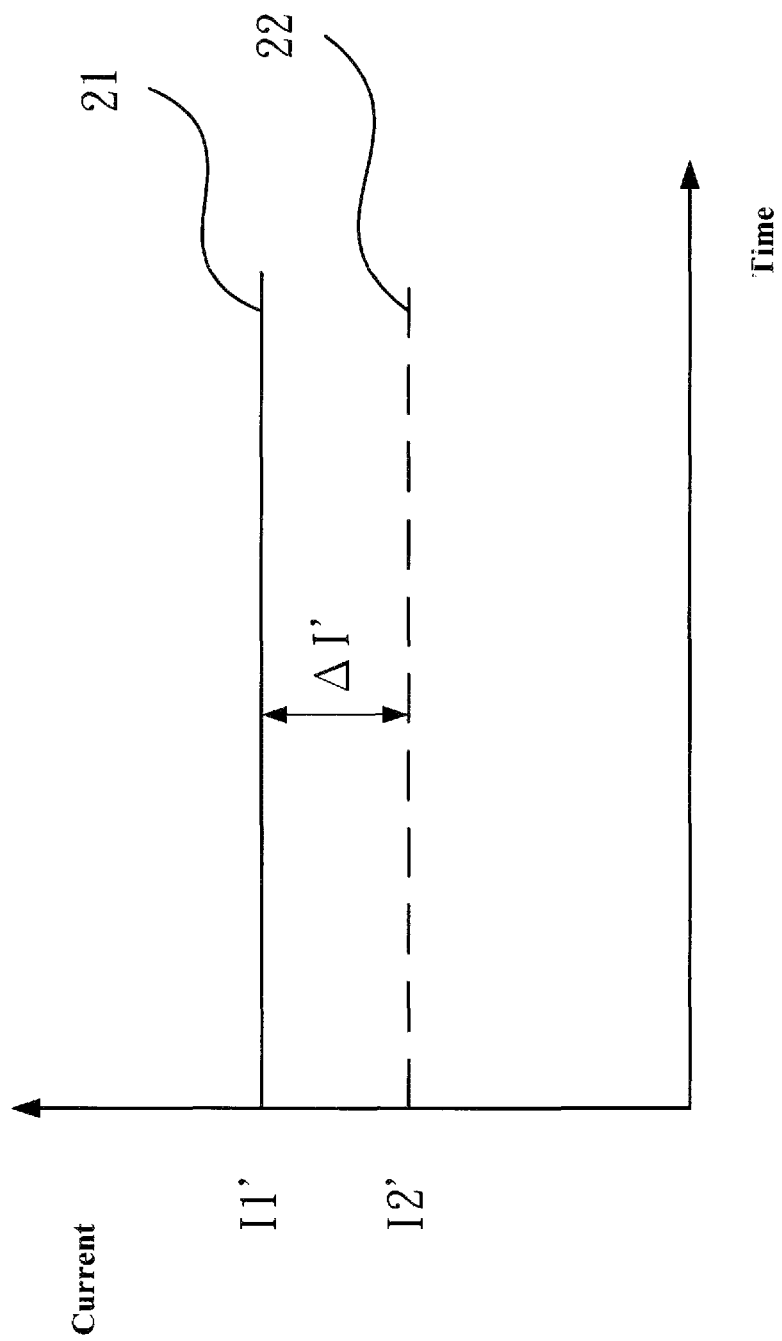
FIG. 5 is a diagram showing the second state signal output of the refractive fuel concentration detector according to a first embodiment of the invention.

FIG. 4 is a schematic diagram showing the component layout and the second state of the refractive fuel concentration detector according to a first embodiment of the invention. FIG. 5 is a diagram showing the second state signal output of the refractive fuel concentration detector according to a first embodiment of the invention. Referring to FIG. 4 and FIG. 5, when the concentration of fuel (22a) is in a second state, the first refracted light (4) forms a displacement D' in the fuel (22a) such that the first light sensor (11a) and the second light sensor (11b) would respectively output a corresponding current 11' and current 12' based on the dose of light received. The circuit device (13) obtains and outputs electrical signals carrying the current value signals. Subsequently, the computing device (23) of the fuel cell system (2) determines the concentration value of fuel (22a) under second state based on the electrical signals of current value signals.

The array of the plurality of light sensors in the light-sensing device (11) can be arranged in the direction of second refracted light (5) described in the first embodiment. As such, the combination of current value of each light sensor can be converted into corresponding fuel concentration value signals via the computing device (23). The combination of current value of each light sensor indicates the second refracted light (5) is projected onto a location of space in light-sensing device (11). The location of the space is related to the refractivity of fuel, which in turns corresponds to the fuel concentration value. Moreover, the combination of current value of each light sensor can be converted into corresponding fuel concentration value signals based on the value of experimental data or the functional relationship between fuel refractivity and fuel concentration.

Figure 6:
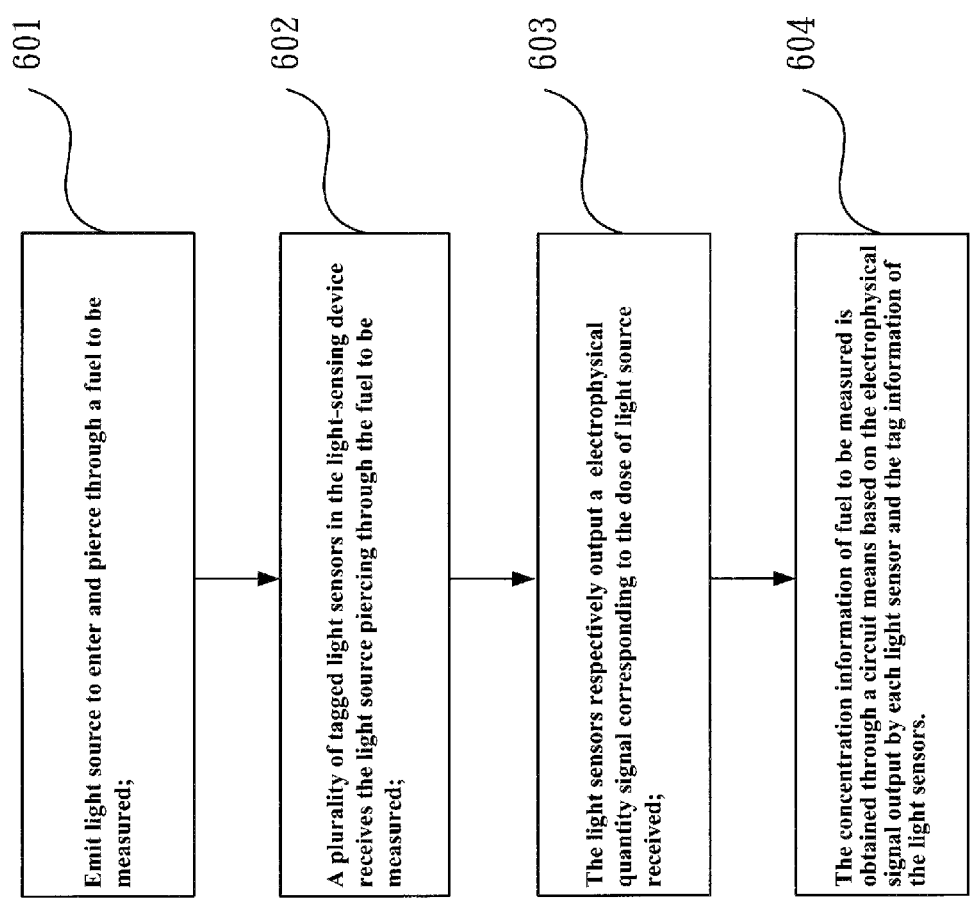
FIG. 6 shows the fuel concentration determination process of the refractive fuel concentration detector according to the invention.

The fuel control device (22) contains an accommodation space (22c) for storing fuel needed for the electrochemical reaction of fuel cell system (2) and residual solution after the reaction. The fuel control device (22) also has a fuel channel (22d) for transporting fuel needed for the electrochemical reaction of fuel cell system (2) and residual solution after the reaction. Moreover, the concentration detector (1) can be arranged inside the accommodation space (22c) or the fuel channel (22d) of fuel control device (22). FIG. 6 shows the fuel concentration determination process of the refractive fuel concentration detector according to the invention. Referring to FIG. 6 and based on the above embodiments, there is provided a refractive fuel concentration detection method used mainly for detecting fuel concentration in the fuel cell system (2). The refractive fuel concentration detection method comprises: step 601—the light source device (12) emits light source to enter and penetrate the fuel (22a) in the fuel control device (22) of fuel cell system (2); step 602—a plurality of tagged light sensors in the light-sensing device (11) receive the light source piercing through the fuel (22a); step 603—each light sensor in the light-sensing device (11) outputs a electrophysical quantity signal corresponding to the dose of light received; and step 604—fuel concentration information of fuel is obtained through a circuit means based on the electrophysical quantity signal output by each light sensor in light-sensing device (11) and the tag information of those light sensors.

Tag information of light sensors refers to information that defines the light sensors, primarily the spatial layout of each light sensor. For example, as shown in FIG. 2 again, first light sensor (11a) and second light sensor (11b) are arranged in the direction of second refracted light (5) with fuel concentration. Those tag information defines the geometric location of each light sensor. Thus based on the electrophysical quantity intensity output by each light sensor corresponding to the dose of light received, coupled with the tag information of each light sensor, the computing device (23) can figure out the location on the light-sensing device (11) at where the second refracted light (5) is projected, and further, obtain the refractivity of first refracted light (4) that pierces through the fuel (22a), and corresponding to which, obtain the concentration information of fuel (22a).

Figure 7:
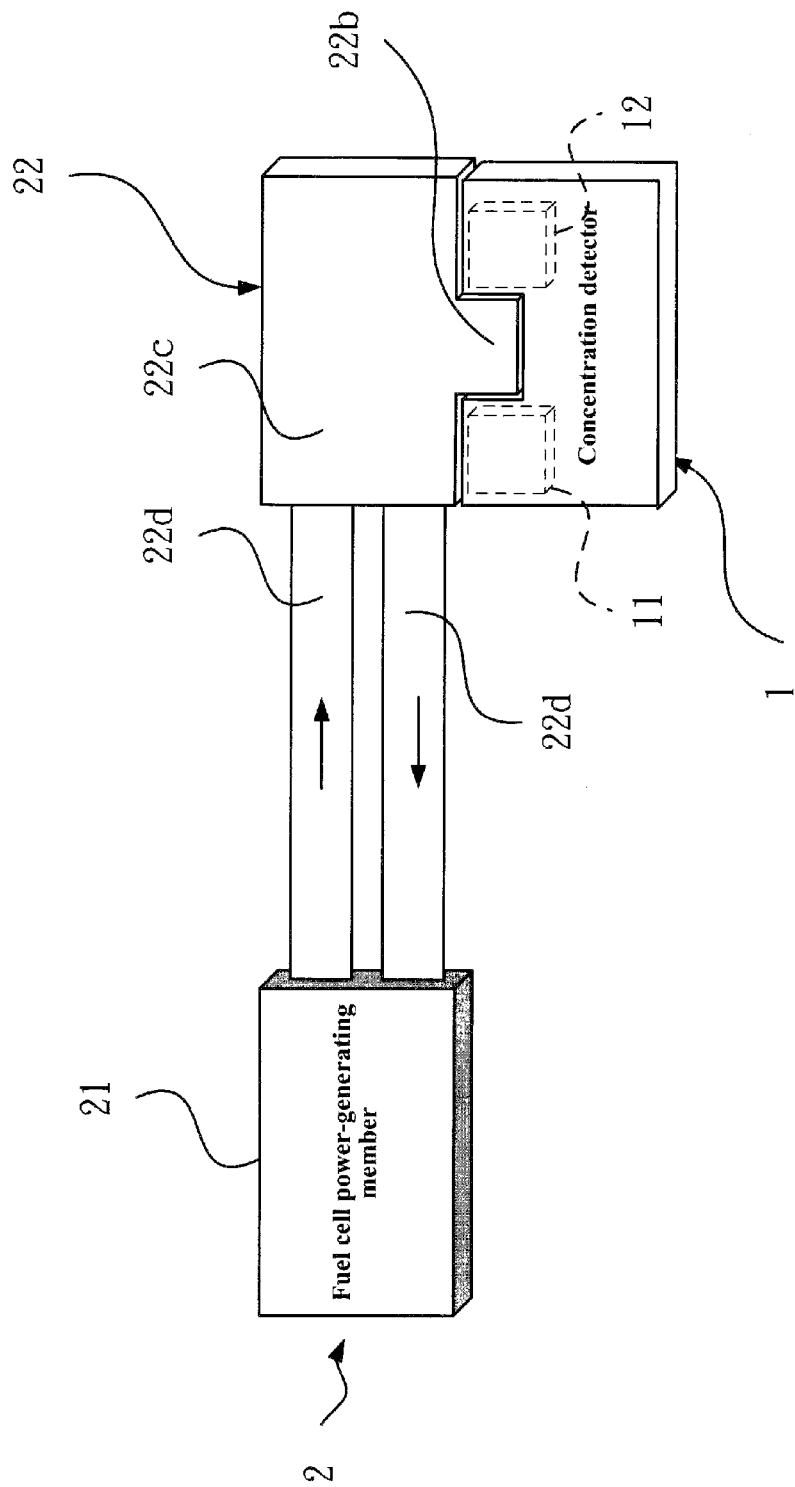
FIG. 7 is a diagram showing the component layout of the refractive fuel concentration detector according to a second embodiment of the invention.

FIG. 7 is a diagram showing the component layout of the refractive fuel concentration detector according to a second embodiment of the invention. In this preferred embodiment, a part of accommodation space (22c) in the fuel control device (22) extends to form a detecting member (22b). At least two sides of the detecting member (22b) are made of material that allows the penetration of infrared light and correspond to the light-sensing device (11) and light source device (12) of the concentration detector (1). The light-sensing device (11) and light source device (12) of concentration detector (1) are respectively arranged on each side of the detecting member (22b) of fuel control device (22). As such, the concentration detector (1) can obtain the fuel concentration in the detecting member (22b) of fuel control device (22) as described in the embodiments.

Figure 8:
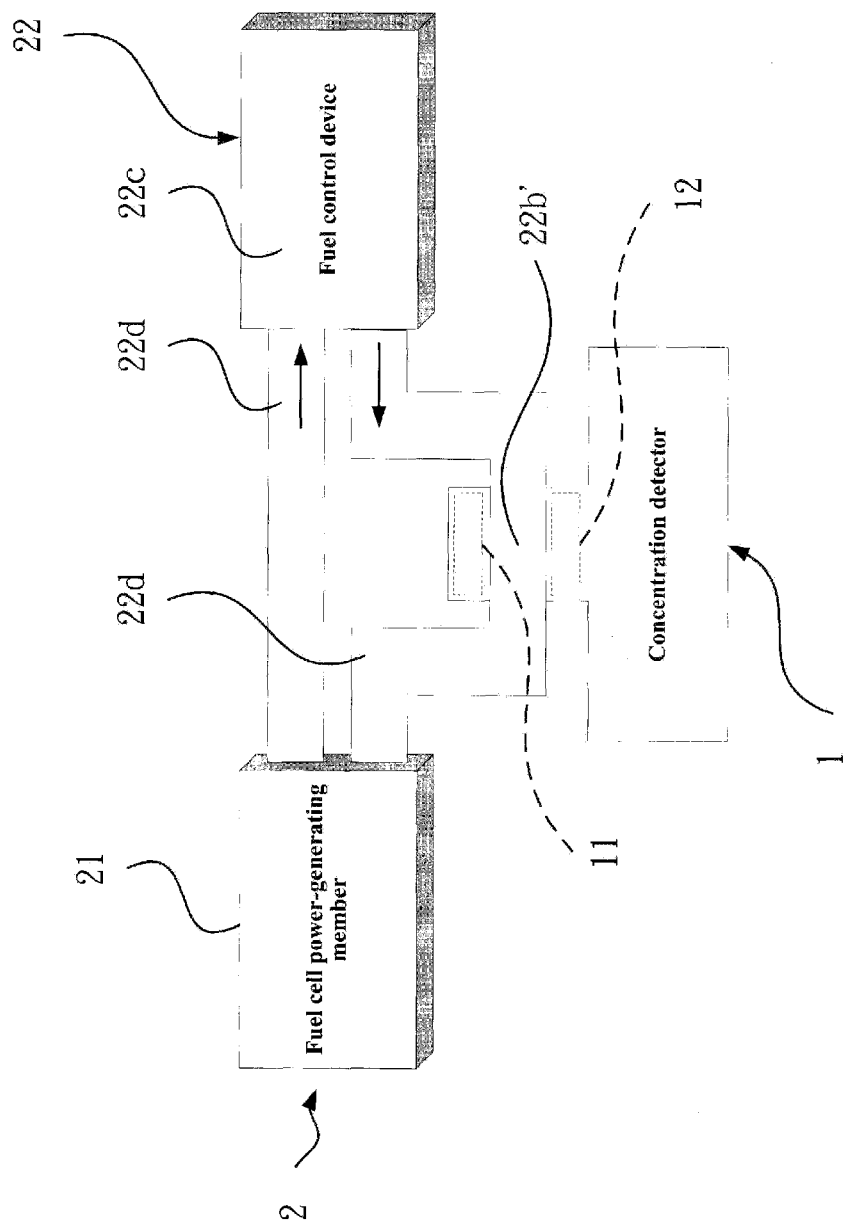
FIG. 8 is a diagram showing the component layout of the refractive fuel concentration detector according to a third embodiment of the invention.

FIG. 8 is a diagram showing the component layout of the refractive fuel concentration detector according to a third embodiment of the invention. In this preferred embodiment, a part of the fuel channel (22d) in the fuel control device (22) forms a detecting member (22b'). At least two sides of the detecting member (22b') are made of material that allows the penetration of infrared light and correspond to the light-sensing device (11) and light source device (12) of the concentration detector (1). The light-sensing device (11) and light source device (12) of concentration detector (1) are respectively arranged on each side of the detecting member (22b') of fuel control device (22). As such, the concentration detector (1) can obtain the fuel concentration in the detecting member (22b') of fuel control device (22).

The preferred embodiments of the present invention have been disclosed in the examples. However these examples should not be construed as a limitation on the actual applicable scope of the invention, and as such, all modifications and alterations without departing from the spirits of the invention and appended claims shall remain within the protected scope and claims of the invention.

What is claimed is:

1. A refractive fuel concentration detector used primarily for the detection of fuel concentration in the fuel control device of a fuel cell system, the refractive fuel concentration detector comprising:

a light source device;

a light-sensing device comprising a plurality of light sensors spaced from each other, the light sensors, while under the state of illumination, respectively outputting a corresponding electrophysical quantity signal based on the dose of light received;

wherein the light source device and the light-sensing device are correspondingly disposed on opposite sides of the fuel control device such that the incident light from light source device can pierce through the fuel with a first refraction on entering the fuel and a second refraction on leaving the fuel and sensed by the light sensors in light-sensing device, each light sensor respectively outputting a corresponding electrophysical quantity signal based on the state of illumination, and the electrophysical quantity signal being corresponding to the fuel concentration;

a circuit device capturing the eleetrophysical quantity singnal output by each light sensor corresponding to the state of illumination and based on the location of the light sensors and the comparative electrophysical quantity intensitv between the sensors, computing corresponding fuel concentration information.

2. The refractive fuel concentration detector according to claim 1, wherein the electrophysical quantity signal output by each light sensor based on the state of illumination is a current value, a voltage value or a resistance value.

3. A refractive fuel concentration detector used primarily in a fuel cell system, the refractive fuel concentration detector comprising:

a fuel control device for storing and transporting fuel needed for the electrochemical reaction of fuel cell system and residual solution after the reaction;

a light source device;

a light-sensing device comprising a plurality of light sensors spaced from each other, the light sensors, while under the state of illumination, respectively outputting a corresponding electrophysical quantity signal based on the dose of light received;

wherein the light source device and the light-sensing device are correspondingly disposed on opposite sides of the fuel control device such that the incident light from light source device has a first refraction on entering the fuel and a second refraction on leaving the fuel, when piercing through the fuel of the fuel control device and projects onto the light sensors in the light-sensing device, a circuit device capturing the electrophysical quantity signal output by each light sensor corresponding to the state of illumination, and based on the location of the light sensors and the comparable electrophysical quantity intensity between the sensors, computing corresponding fuel concentration information.

4. The refractive fuel concentration detector according to claim 3, wherein the electrophysical quantity signal output by each light sensor based on the state of illumination is a current value, a voltage value or a resistance value.

5. The refractive fuel concentration detector according to claim 3, wherein the fuel control device further comprising a fuel channel; and the light source device and the light-sensing device are opposingly disposed on each side of the fuel channel such that the incident light from light source device can refract after piercing through the fuel of the fuel channel and project onto the light sensors in light-sensing device.

6. The refractive fuel concentration detector according to claim 5, wherein the electrophysical quantity signal output by each light sensor corresponding to the state of illumination is a current value, a voltage value or a resistance value.

7. The refractive fuel concentration detector according to claim 3, wherein the plurality of light sensors of the light-sensing device are arranged according to the direction of incidental light from light source device that changes in response to different fuel concentrations, and arranged in the light-sensing device.

8. The refractive fuel concentration detector according to claim 7, wherein the circuit device computes the corresponding fuel concentration information based on the location of light sensors and the corresponding electrophysical. quantity intensity; the algorithm of circuit device uses either the value of experimental data or the functional relationship between fuel refractivity and fuel concentration.

9. The refractive fuel concentration detector according to claim 1, wherein the light source supplied by the light source device is infrared light, visible light or single-frequency light.

10. A refractive fuel concentration detection method used primarily for detection of fuel concentration in a fuel cell system, comprising the steps of:

emitting light from a light source into a fuel and piercing through the fuel with a first refraction on entering the fuel and a second refraction on leaving the fuel;

receiving the light source piercing through the fuel through a plurality of tagged light sensors spaced from each other in a light-sensing device;

the light sensors respectively outputting a electrophysical quantity signal corresponding to the dose of light source received; and using a circuit means to obtain concentration information of fuel based on the comparative electrophysical quantity signal output by each light sensor and the tag information of light sensors;

wherein the circuit device computes and obtains concentration information of fuel based on the comparative electrophysical quantity signal output by each light sensor and the tag information of the light sensor; the algorithm of circuit device uses either the value of experimental data or the functional relationship between fuel refractivity and fuel concentration.

11. The refractive fuel concentration detection method according to claim 10, wherein the electrophysical quantity signal output by each light sensor based on the dose of light source received is a current value, a voltage value or a resistance value.

12. The refractive fuel concentration detection method according to claim 10, wherein the tag information of each light sensor in the light-sensing device is the layout location of the light sensor.

13. The refractive fuel concentration detection method according to claim 12, wherein the layout location of each light sensor of the light-sensing device is arranged according to the direction of incidental light from light source device that changes in response to different fuel concentrations, and arranged in the light-sensing device.

14. The refractive fuel concentration detection method according to claim 10, wherein in the process of using a circuit means to obtain concentration information of fuel based on the electrophysical quantity signal output by each light sensor and the tag information of the light sensor, it compares the electrophysical quantity signal respectively output by a first light sensor and a second light sensor in the light sensors and obtains the fuel concentration information.

15. The refractive fuel concentration detection method according to claim 14, wherein the tag information of the first light sensor and the second light sensor is their layout location.

16. The refractive fuel concentration detection method according to claim 15, wherein the layout location of the first light sensor and the second light sensor are arranged according to the direction of incidental light from light source device that changes in response to different fuel concentrations, and arranged in the light-sensing device.

* * * * *